United States Patent
Pasquino et al.

(10) Patent No.: US 11,896,486 B2
(45) Date of Patent: Feb. 13, 2024

(54) DELIVERY SYSTEM FOR TRANSCATHETER PROSTHETIC HEART VALVES

(71) Applicant: Epygon, Paris (FR)

(72) Inventors: Enrico Pasquino, Savigny (CH);
Marcio Scorsin, Luxembourg (LU);
Andrea Marchisio, Ivrea (IT); Lorenzo Valerio, Moriago della Battaglia (IT);
Stefano Pasquino, Savigny (CH)

(73) Assignee: EPYGON, Paris (FR)

( * ) Notice: Subject to any disclaimer, the term of this patent is extended or adjusted under 35 U.S.C. 154(b) by 477 days.

(21) Appl. No.: 16/490,640

(22) PCT Filed: Mar. 1, 2018

(86) PCT No.: PCT/EP2018/055045
§ 371 (c)(1),
(2) Date: Sep. 3, 2019

(87) PCT Pub. No.: WO2018/162317
PCT Pub. Date: Sep. 13, 2018

(65) Prior Publication Data
US 2020/0000589 A1    Jan. 2, 2020

(30) Foreign Application Priority Data

Mar. 8, 2017 (EP) .................................... 17159957

(51) Int. Cl.
*A61F 2/24* (2006.01)
*A61B 17/00* (2006.01)
(Continued)

(52) U.S. Cl.
CPC .......... *A61F 2/2439* (2013.01); *A61F 2/2427* (2013.01); *A61F 2/2433* (2013.01);
(Continued)

(58) Field of Classification Search
None
See application file for complete search history.

(56) References Cited

U.S. PATENT DOCUMENTS

| 4,811,737 A | 3/1989 | Rydell |
| 5,728,065 A | 3/1998 | Follmer et al. |

(Continued)

FOREIGN PATENT DOCUMENTS

| WO | 2008/031103 A2 | 3/2008 |
| WO | WO 2008/031103 A2 | 3/2008 |

(Continued)

OTHER PUBLICATIONS

International Search Report dated Oct. 5, 2018 forn PCT/EP2018/055045.
(Continued)

*Primary Examiner* — Shaun L David
(74) *Attorney, Agent, or Firm* — Finch & Maloney PLLC

(57) ABSTRACT

Transcatheter delivery system for a self-expandable heart valve prosthesis (29) comprising a handle (17, 17'), a hollow shaft (6) a distal tip (1, 1", 1'") and an actuation mechanism for moving a valve prosthesis (29) towards said distal tip (1, 1", 1'") or said handle (17, 17'), said hollow shaft (6) being adapted to slidingly receive a compressed valve prosthesis (29); the system being characterized by the fact that it includes a valve prosthesis crimping tool that comprises a hollow conical element (21), a detachable transfer tube (24) and a pulling device (26); said conical element (21) being adapted to let a valve prosthesis (29) in an expanded state enter the conical element (21) through its basis and enter said transfer tube (24) in a compressed state, said valve prosthesis (29) being pulled by said pulling device (26) when crossing said conical element (21) and entering said
(Continued)

transfer tube (24), said transferring tube (24) being adapted to be temporarily connected to said conical element (21).

19 Claims, 32 Drawing Sheets

(51) Int. Cl.
*A61F 2/95* (2013.01)
*A61F 2/962* (2013.01)

(52) U.S. Cl.
CPC .. *A61F 2/2436* (2013.01); *A61B 2017/00243* (2013.01); *A61F 2/9517* (2020.05); *A61F 2/9525* (2020.05); *A61F 2/962* (2013.01); *A61F 2002/9505* (2013.01)

(56) References Cited

U.S. PATENT DOCUMENTS

| | | | |
|---|---|---|---|
| 6,514,264 B1 | 2/2003 | Naglreiter | |
| 8,568,472 B2 | 10/2013 | Marchand et al. | |
| 9,554,897 B2 | 1/2017 | Lane et al. | |
| 2003/0139795 A1* | 7/2003 | Olson | A61F 2/95 623/1.11 |
| 2008/0071361 A1 | 3/2008 | Tuval et al. | |
| 2009/0192601 A1* | 7/2009 | Rafiee | A61M 5/007 623/2.11 |
| 2010/0256749 A1* | 10/2010 | Tran | A61F 2/0095 623/2.11 |
| 2010/0298931 A1* | 11/2010 | Quadri | A61F 2/2439 623/2.11 |
| 2013/0079872 A1* | 3/2013 | Gallagher | A61F 2/2436 623/2.11 |
| 2013/0123757 A1 | 5/2013 | Crisostomo et al. | |
| 2014/0309731 A1 | 10/2014 | Quadri et al. | |
| 2014/0330368 A1* | 11/2014 | Gloss | A61F 2/243 623/2.11 |
| 2014/0343670 A1 | 11/2014 | Bakis et al. | |
| 2015/0173895 A1 | 6/2015 | Shipley et al. | |
| 2015/0182334 A1 | 7/2015 | Bourang et al. | |
| 2016/0228251 A1* | 8/2016 | Nyuli | A61F 2/2436 |
| 2016/0302921 A1* | 10/2016 | Gosal | A61F 2/2427 |
| 2018/0133007 A1* | 5/2018 | Prabhu | A61M 25/0147 |

FOREIGN PATENT DOCUMENTS

| | | |
|---|---|---|
| WO | 2013/120181 A1 | 8/2013 |
| WO | WO 2013/120181 | 8/2013 |
| WO | 2014/121280 A2 | 8/2014 |
| WO | WO 2014/121280 | 8/2014 |
| WO | 2015/004173 A1 | 1/2015 |
| WO | WO 2015/004173 A1 | 1/2015 |

OTHER PUBLICATIONS

Written Opinion dated Oct. 5, 2018 forn PCT/EP2018/055045.
Written Opinion and International Search Report for PCT/2018/055045 dated Oct. 5, 2018.
Korean Office Action Corresponding to 10-2019-7029401 dated Jan. 2, 2023.

* cited by examiner

Figure 1:
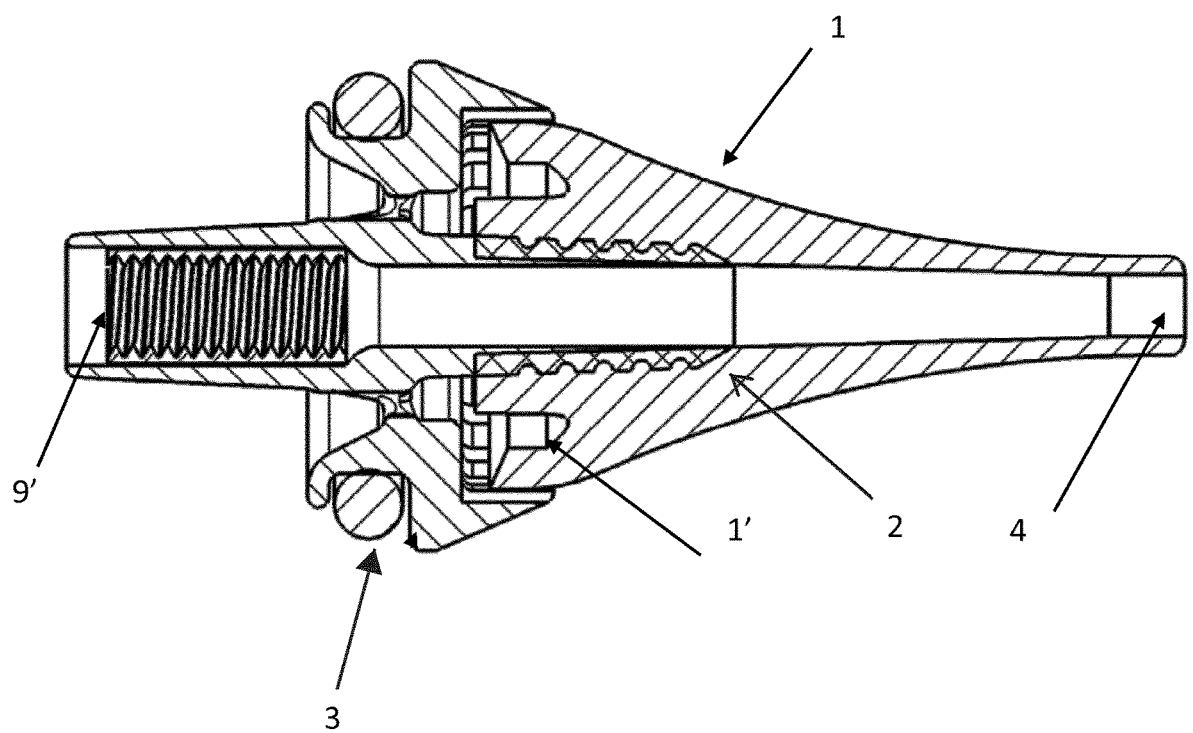

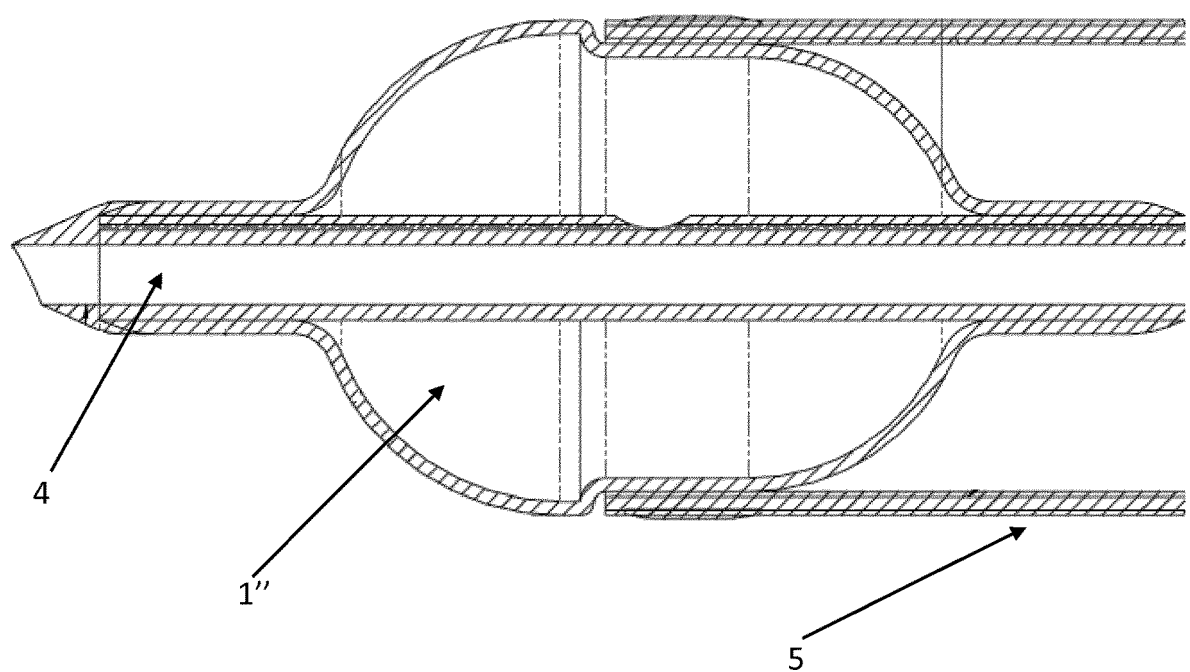
Fig. 1.1

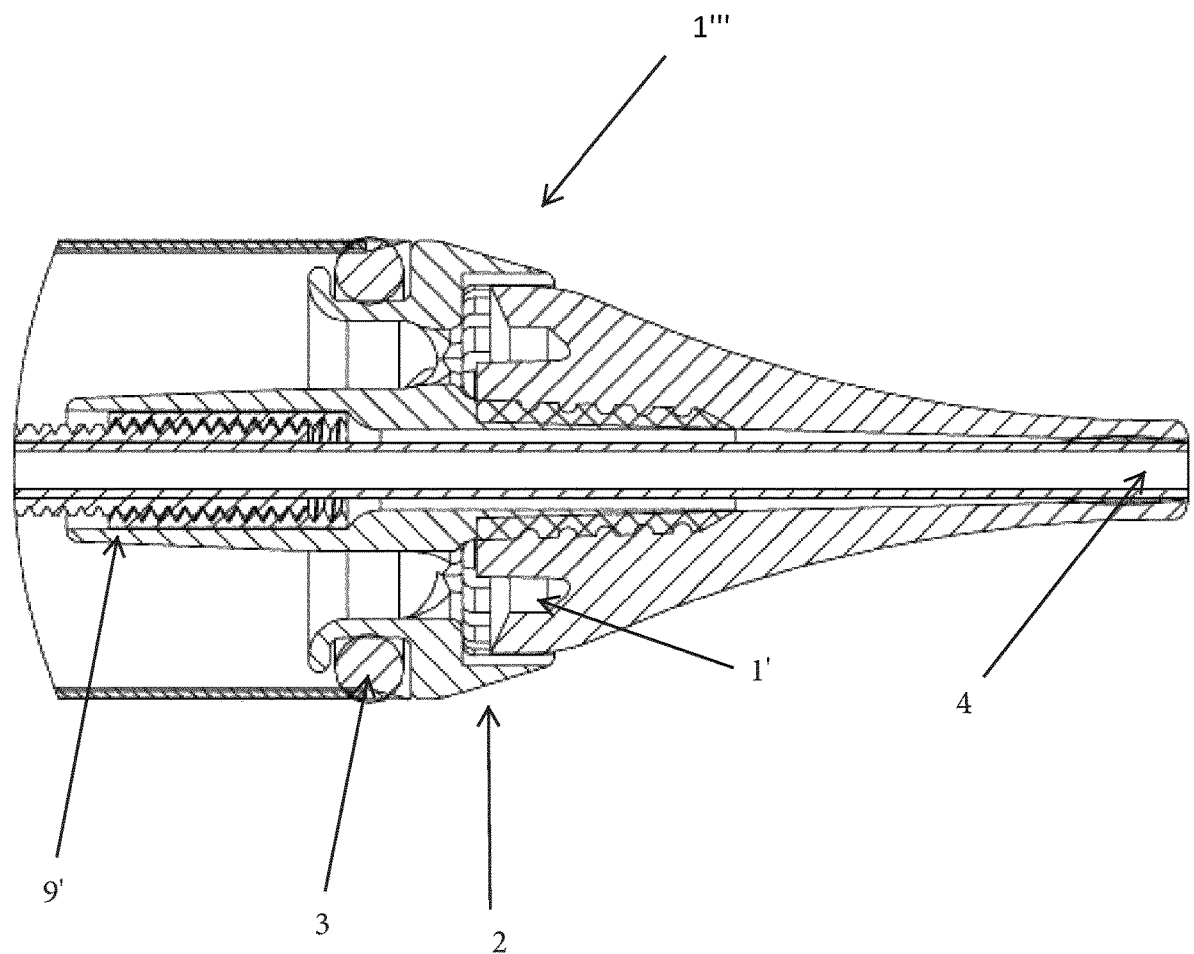
Fig. 1.2

Figure 3:
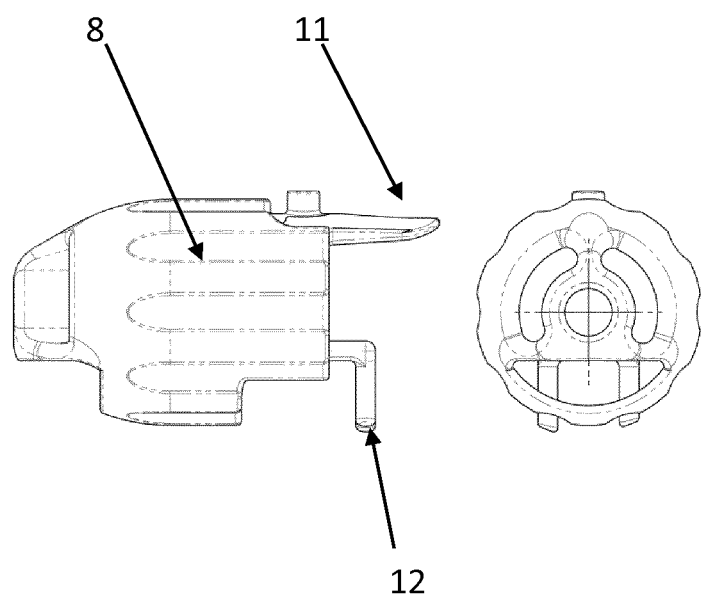

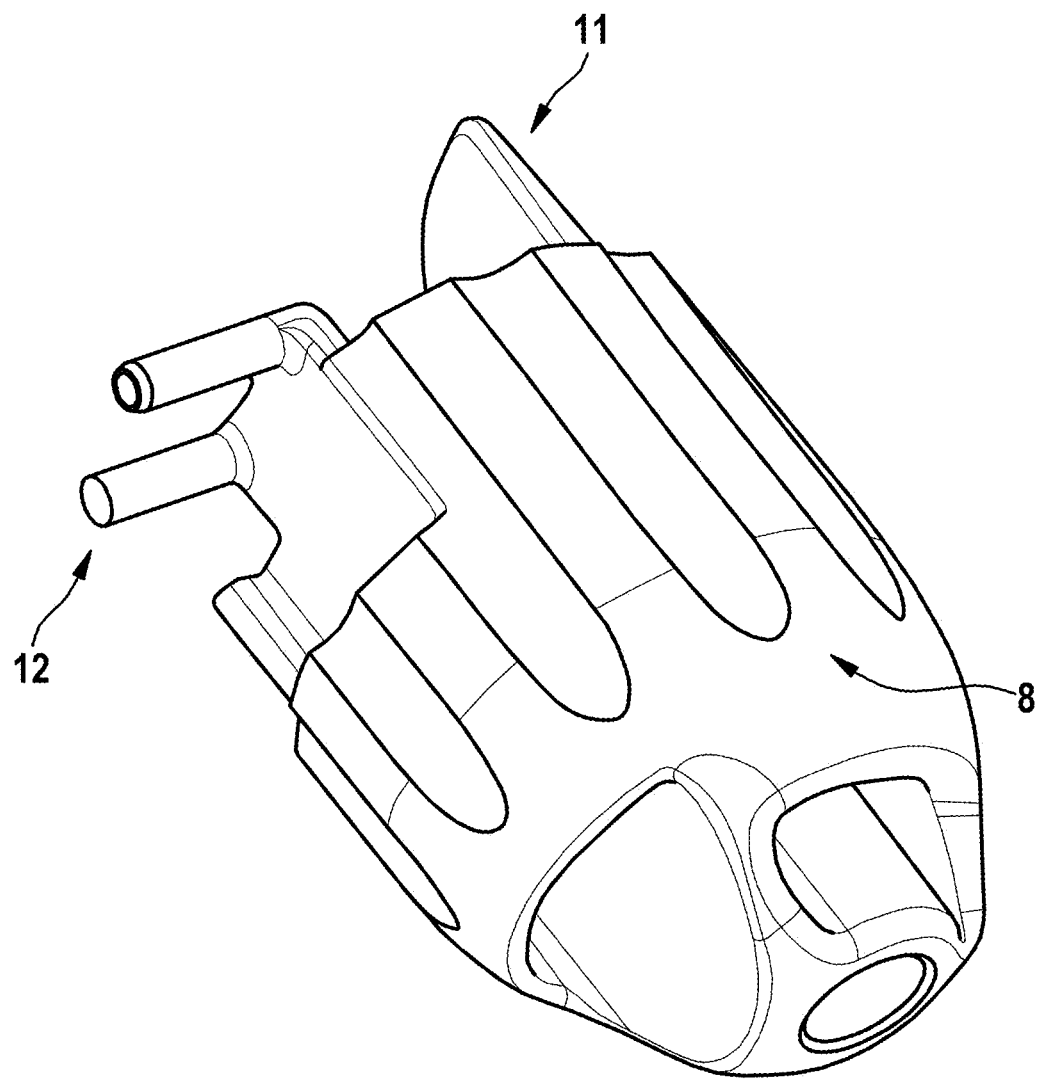
Fig. 3.1

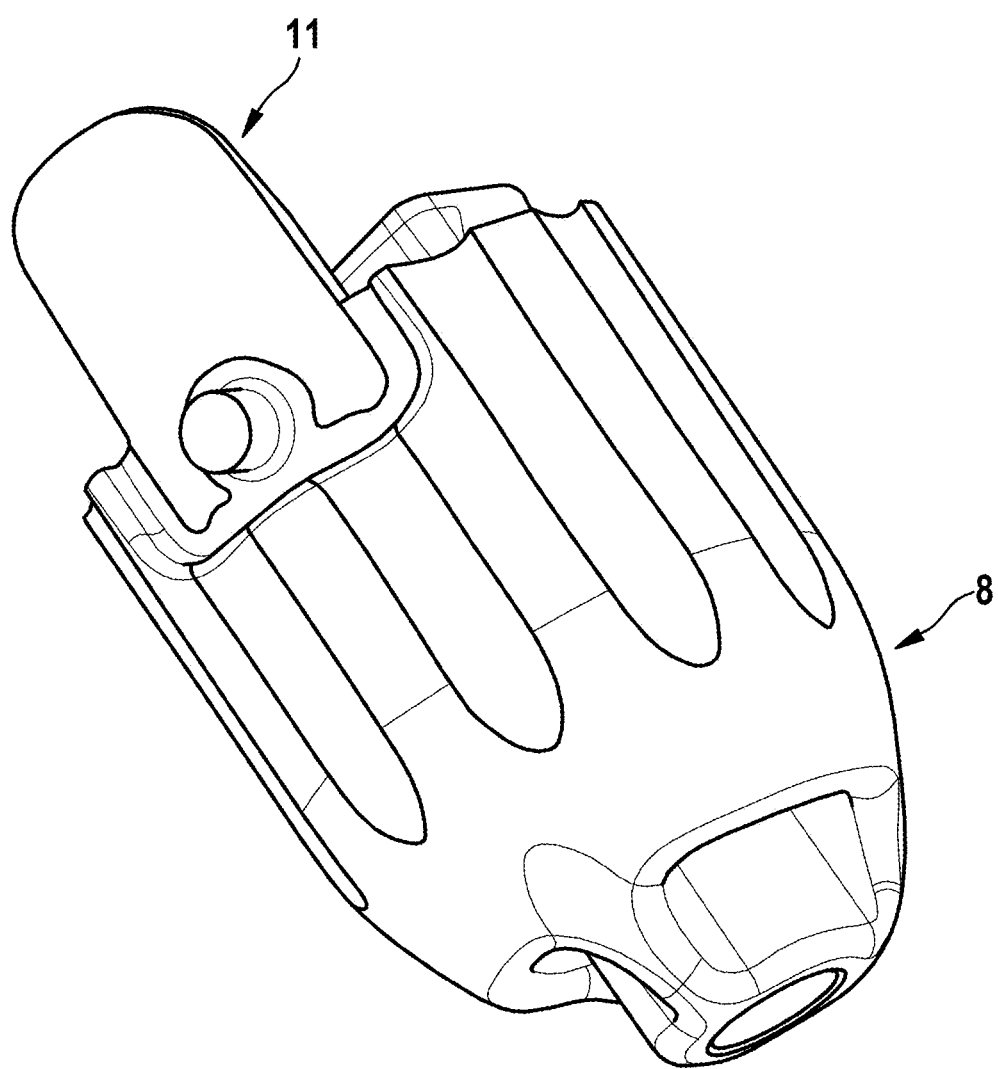
Fig. 3.2

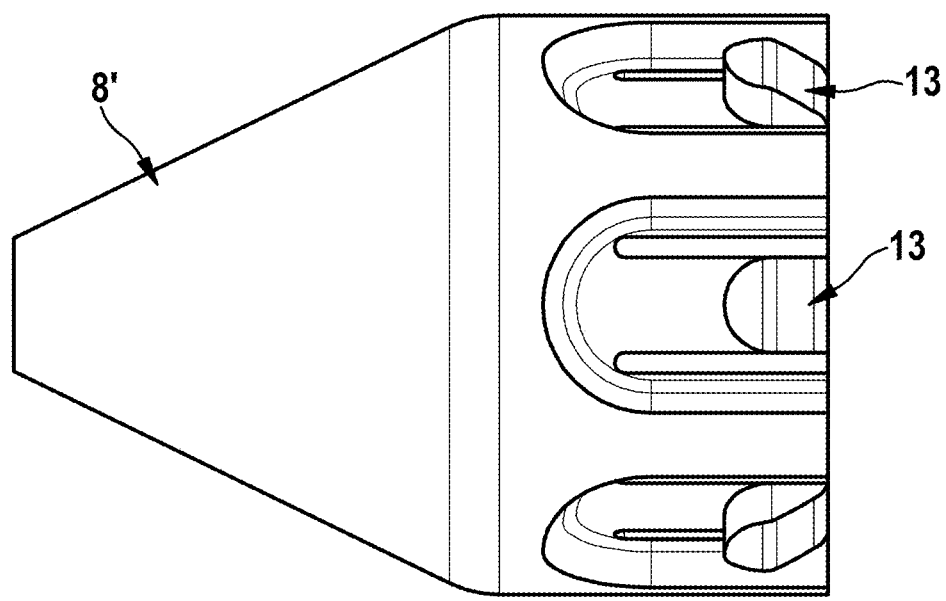
Fig. 4
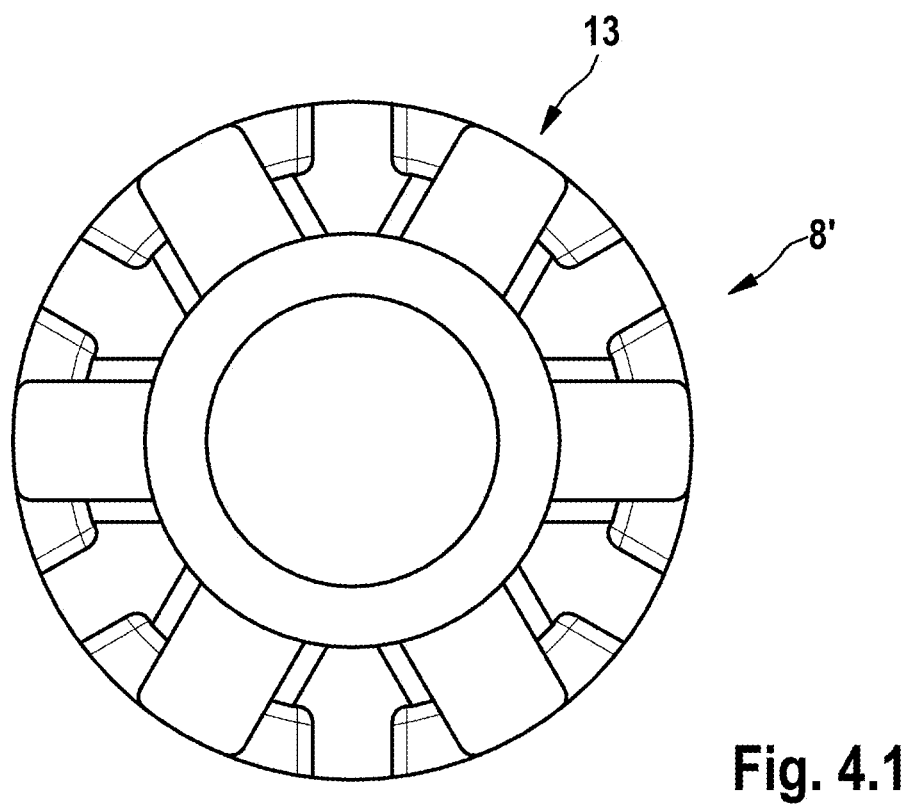
Fig. 4.1

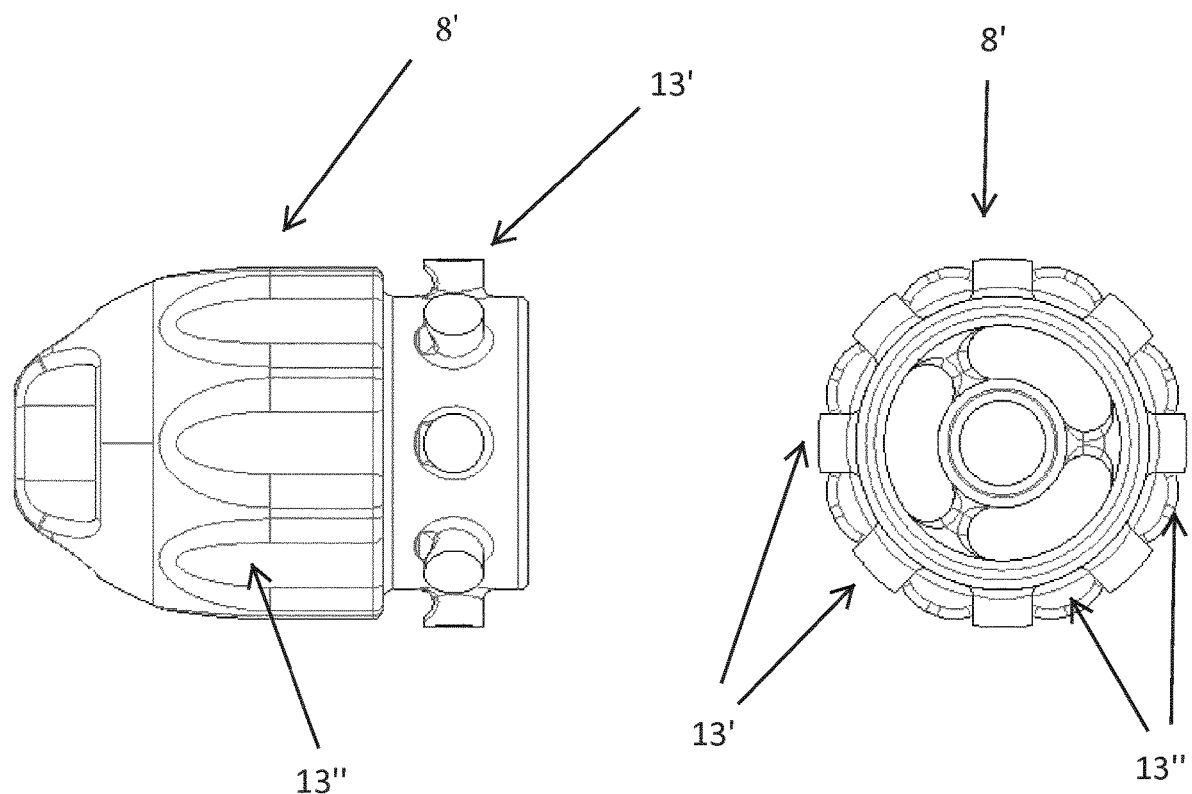
Fig. 4.2

Figure 5:
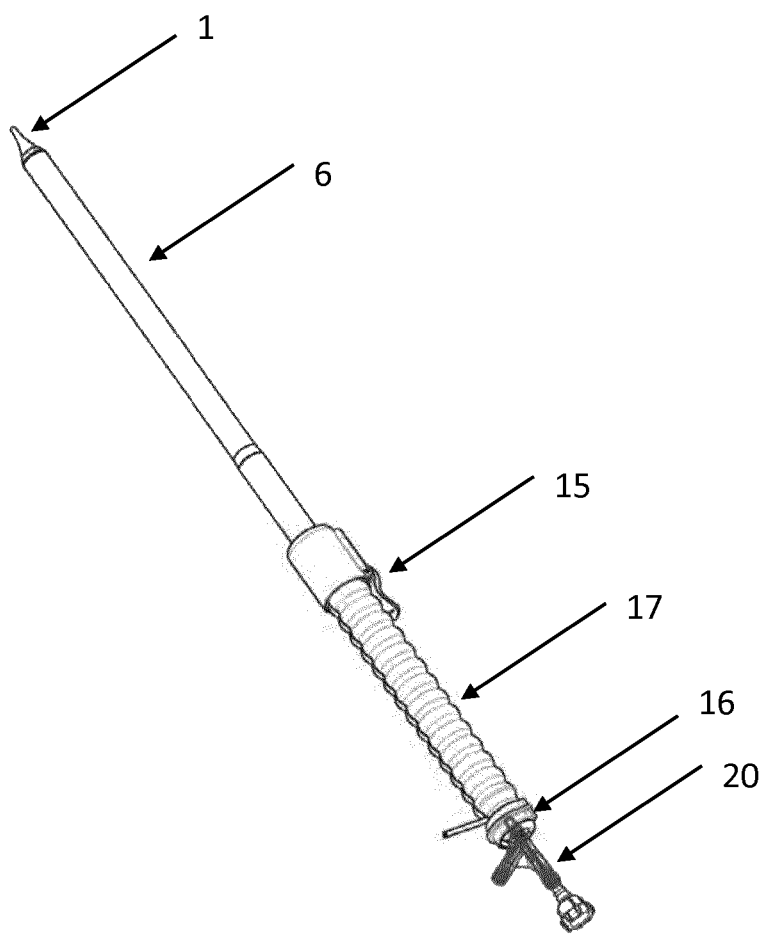

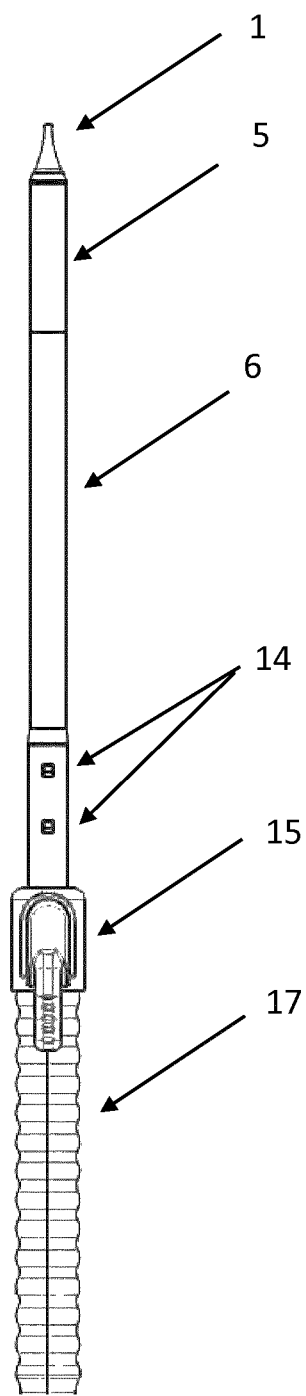
Fig. 5.1

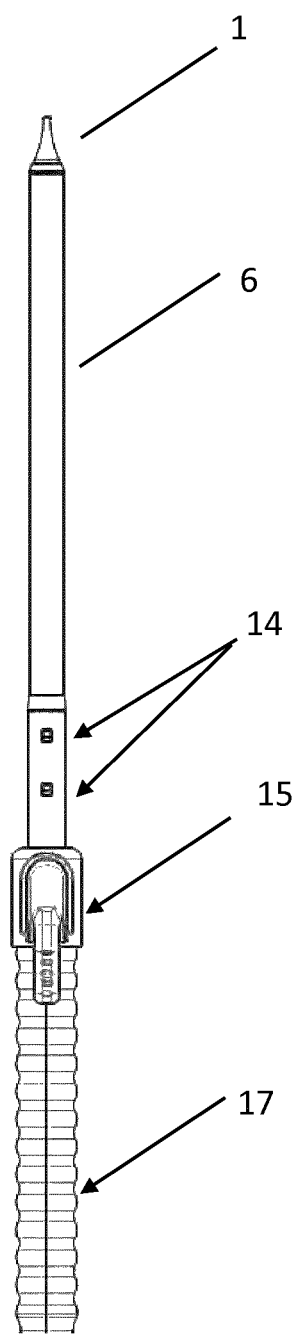
Fig. 5.2

Figure 6:
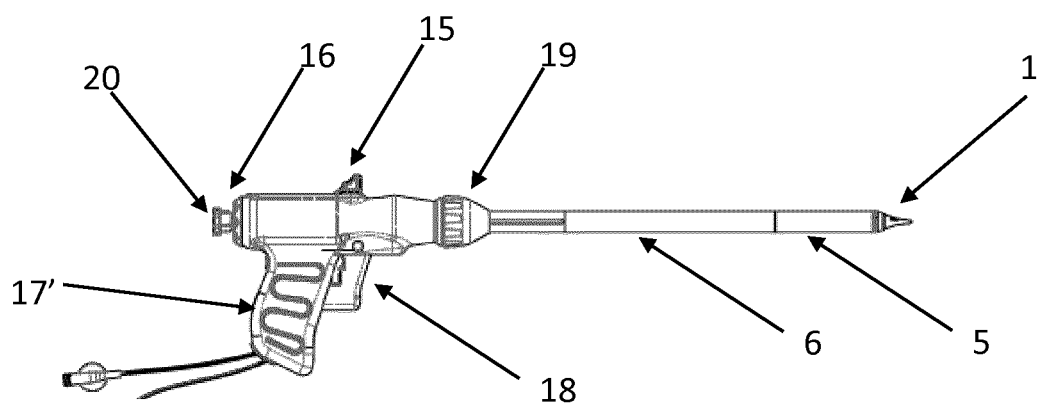

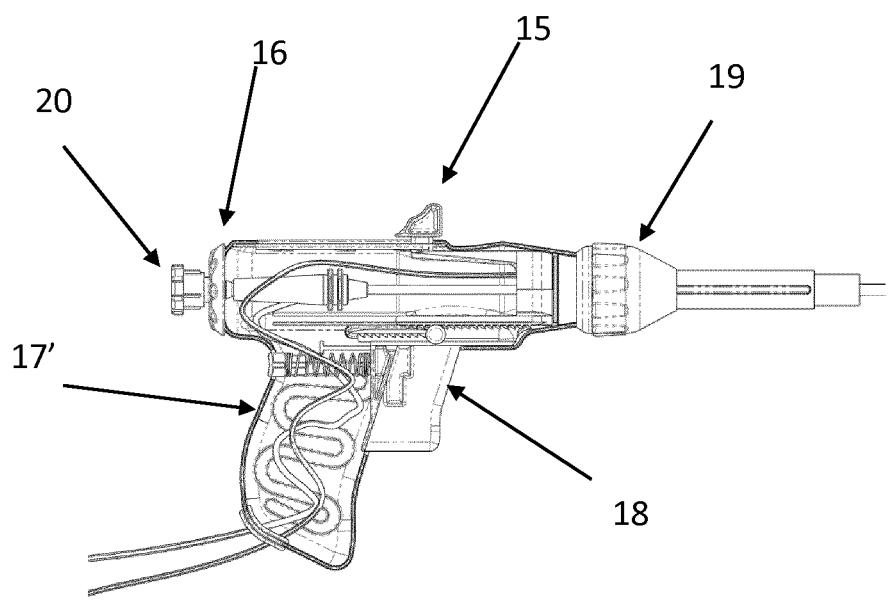
Fig. 6.1

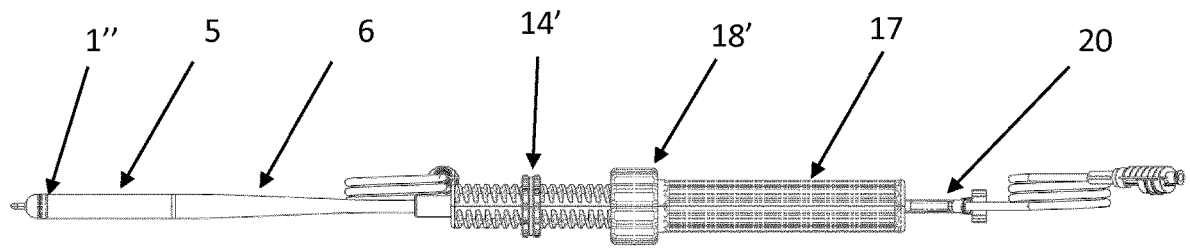
Fig. 6.2
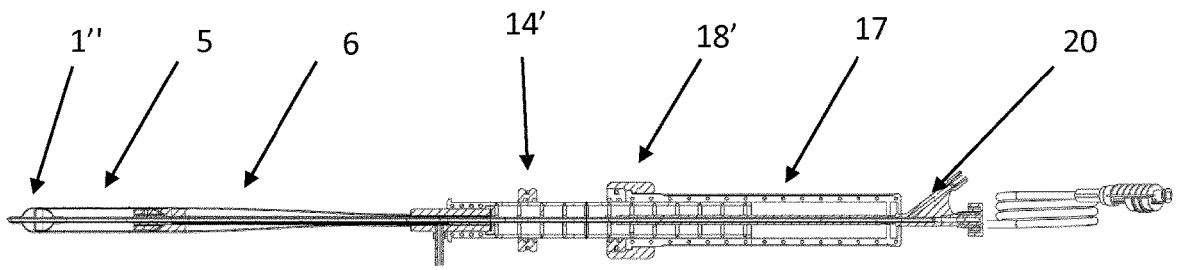
Fig. 6.3

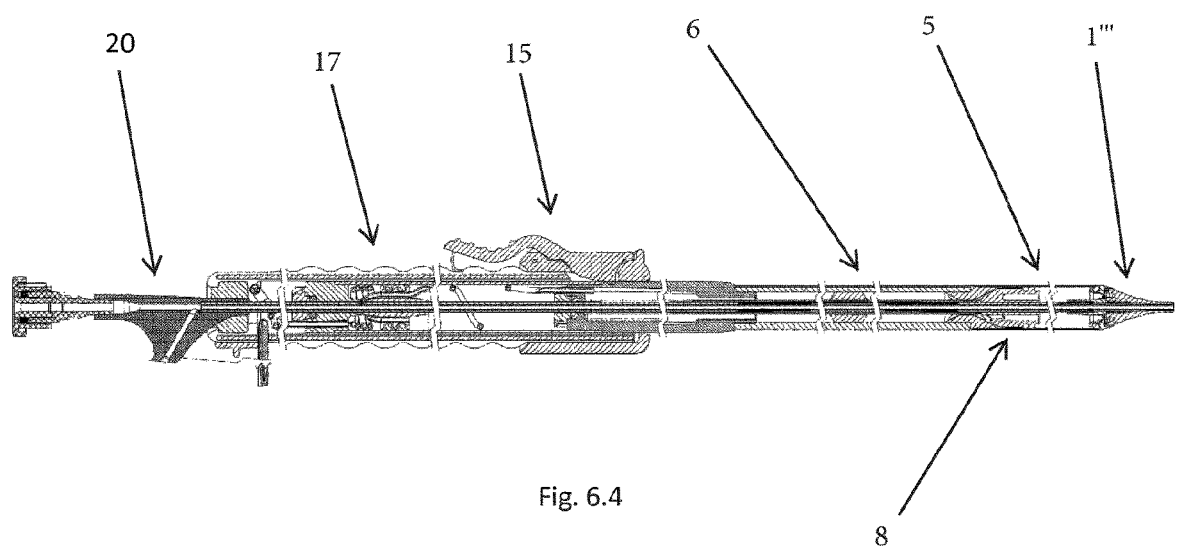
Fig. 6.4

Figure 7:
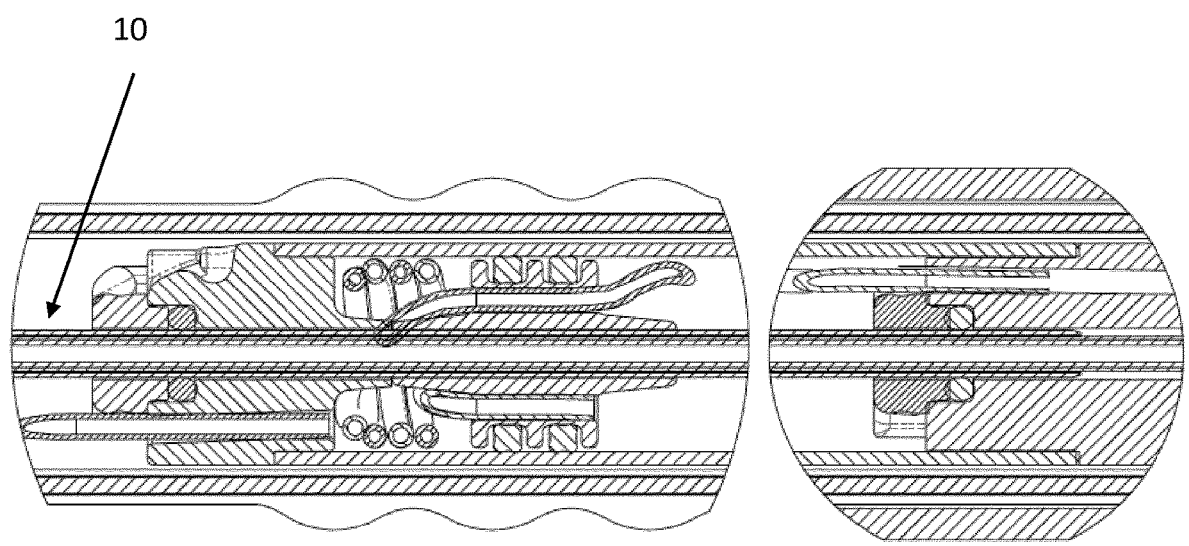

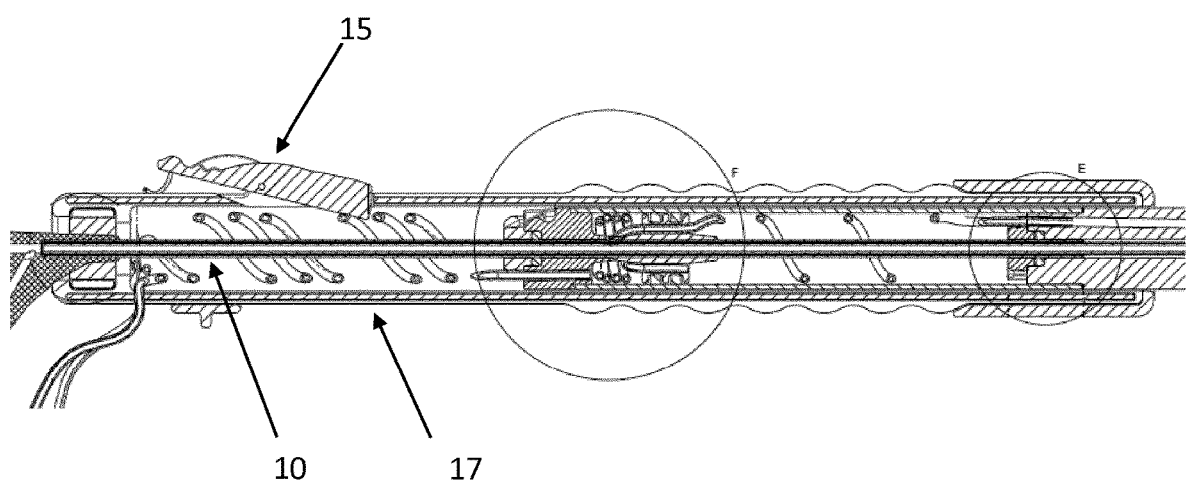
Fig. 7.1

23

23

23

23

DELIVERY SYSTEM FOR TRANSCATHETER PROSTHETIC HEART VALVES

CROSS REFERENCE TO RELATED APPLICATIONS

The present application is a United States national stage application of International patent application PCT/EP2018/055045 filed on Mar. 1, 2018 designating the United States, and claims foreign priority to European patent application EP 17159957.4 filed on Mar. 8, 2017, the contents of both documents being herewith incorporated by reference in their entirety.

FIELD OF INVENTION

The present invention relates to transcatheter delivery of self-expandable heart valve prostheses.

STATE OF THE ART

Heart valve prostheses replace the native valve function. They open and close during a cardiac cycle, directing the blood flow through the heart chambers and out to the rest of the body. The semilunar valves (aortic and pulmonary) are flaps of endocardium and connective tissue reinforced by fibers, which prevent the valves from turning inside out. They are shaped like a half moon, hence the name semilunar. The semilunar valves are located between the aorta and the left ventricle, and between the pulmonary artery and the right ventricle. On the contrary the atrio-ventricular valves (mitral and tricuspid) are thin structures that are composed of endocardium and connective tissue. They are located between the atria and the ventricles. The mitral valve represents the anatomical feature that regulates the blood passage between the left atrium and the left ventricle. It prevents the blood in the ventricle from returning to the atrium and consists of two triangular flaps attached at their bases to the fibrous ring, which surrounds the opening and connected at their margins with the ventricular walls by the chordae tendinae and papillary muscles.

The major issues related to mitral valve impairment consist in stenosis or insufficiency of the valve. The latter, which eventually leads to mitral regurgitation, results in a leakage of blood backward through the mitral valve each time the left ventricle contracts. In particular, a leaking mitral valve allows blood to flow in two directions during the contraction. Some blood flows from the ventricle through the aortic valve—as it should—and some blood flows back into the atrium. Leakage can increase blood volume and pressure in the area. The increased blood pressure in the left atrium can increase pressure in the veins leading from the lungs to the heart (pulmonary veins). Moreover, if regurgitation is severe, increased pressure may result in lungs' congestion (or fluid build-up). Solutions have been developed to restore the correct valve continence and consist in surgical valve annuloplasty or treatment of leaflet prolapse. To reduce the burden of open chest surgical approaches, lately noninvasive repairing techniques have been introduced. Besides such approach helps reducing the valve insufficiency initially, several studies reported as the benefits of this technique were no better than traditional mitral valve surgery, with the need of late reoperation for several patients. These outcomes underline how is necessary to develop an entire prosthetic valve able to substitute the entire native functional element with a non-invasive implanting procedure. Although solutions have been proposed to substitute native aortic valves with percutaneous transcatheter artificial valves, the distinctive positioning and hemodynamic features of a mitral valve have discouraged such implanting approach so far. In order to deploy self-expandable valves through a transcatheter approach, specific delivery systems have been developed.

The development of self-expandable valves allows crimping the valvular structure into a cylindrical shaft prior to deploy the valve in the correct anatomical position. In addition, several delivery systems allow 1) the charging the valve inside the delivery's shaft in a very precise way without too much traction that could damage the stent structure and with an evenly distributed forces to prevent the overlapping of the stent structures; and 2) the possibility to recapture the prostheses into the shaft if the releasing position is incorrect or the procedure must be aborted for any reason. An example of such a system is disclosed in US patent application 2015/0173895 A1.

It is extremely important to reach and to match the native anatomical annulus prior to release the valve because a displacement of the valve prosthesis with respect to the correct anatomical position may cause several fatal complications as permanent paravalvular leaks or even a dislodgement of the valve from the implant site. The operative mechanisms of delivery systems on the market mainly rely on mechanical solutions. Typically, a series of inner and outer catheters allow pushing and deploying the valves. Rotating crank operated by physicians have the advantage of ensuring the perfect control of the speed during the deployment because each movement are directly transmitted to the shaft allowing a tactile feed-back and absolute control of the necessary force to release the prosthesis. However, during the loading of the collapsed prosthesis inside the delivery, a relative motion among these rigid structures may occur. Such systems are less than ideal because they are time consuming and small variations in the loading phase can occur leading to a no uniform stent distribution inside the shaft, mainly if the stent shape is asymmetric. This aspect may have significant consequences because during the procedure the prosthesis may be asymmetrically released and not be properly positioned.

Delivery systems with hydraulic motion have been introduced for deploying vascular stents (U.S. Pat. Nos. 6,514,264; 5,728,065; 4,811,737). Besides complex in structure and comprising several structural elements which may include possible critical issues, such devices introduce an interesting solution that involve the fluid pressure provided by a syringe-like actuator to release the stent in position. Even though it appears clear that there is a need to simplify and improve this concept, its advantage for correctly deploying a transcatheter seems elusive because introduces an interface between the operator and the prosthesis that could diminish the absolute control during deployment. However, the main characteristics of the hydraulic system i.e. low friction, evenly distributed mechanism and discomfort if higher force is necessary would be of great advantages over mechanical deliveries during the loading phase of the prosthesis and whenever a recovery of the valve was necessary. It is imperative that the delivery system must allow the loading and release of the valve in the correct position, implying a high safety and reliability of the device during the procedure. Moreover, the system should allow recovering the valve prior final release whenever it would be necessary.

With respect to the mechanism of actuation, it can consist of at least different types of actuation systems, regardless of the access route to be used. (a) The mechanical delivery system consists in a ring rotating on crank. It has a speed of release, during loading and deployment of the prosthesis that is depending from the distance between the threads of the crank. (b) The hydraulic delivery system has a two-way mechanism. One inlet to deploy the prosthesis and one outlet to load/recover the prosthesis. (c) The third operative system is based on a synergic combination of the two-abovementioned systems. The association of the hydraulic mechanisms to be employed during the loading/recovery phase associated with the mechanical mechanism during the deployment phase of the prosthesis or vice-versa. Therefore, optimizing the procedural process of transcatheter valve implantation.

The implant procedure of transcatheter valve prostheses require to collapse the prosthesis in order to be loaded into the delivery system. The crimping procedure of the prosthesis is performed with a certain number of accessory tools specifically designed.

GENERAL DESCRIPTION OF THE INVENTION

The present invention consists in an improved delivery system that allows the positioning and deployment, via transcatheter approach, of heart valve prostheses, in particular a atrio-ventricular prostheses. The delivery system comprises a crimping tool that reduces in diameter the prosthetic valve. The prosthesis is compressed so that it can be loaded into the valve-cover of the delivery system.

The invention more precisely concerns a transcatheter delivery system for a self-expandable heart valve prosthesis comprising a handle, a hollow shaft a distal tip and an actuation mechanism for moving a valve prosthesis towards said distal tip or said handle, said hollow shaft being adapted to slidingly receive a compressed valve prosthesis; the system being characterized by the fact that it includes a valve prosthesis crimping tool that comprises a hollow conical element, a detachable transfer tube and a pulling device; said conical element being adapted to let a valve prosthesis in an expanded state enter the conical element through its basis and enter said transfer tube in a compressed state, said valve prosthesis being pulled by said pulling device when crossing said conical element and entering said transfer tube, said transferring tube being adapted to be temporarily connected to said conical element, during a crimping procedure, and disconnected from it during a subsequent loading procedure. The delivery system according to the invention is preferably designed to allow an access of the prosthesis via left ventricle apex in transapical access (retrograde), via left atrium in transatrial access (antegrade) or in alternative via the femoral vein and transseptal puncture from right to left atrium (antegrade).

DETAILED DESCRIPTION OF THE INVENTION

Figure 2:
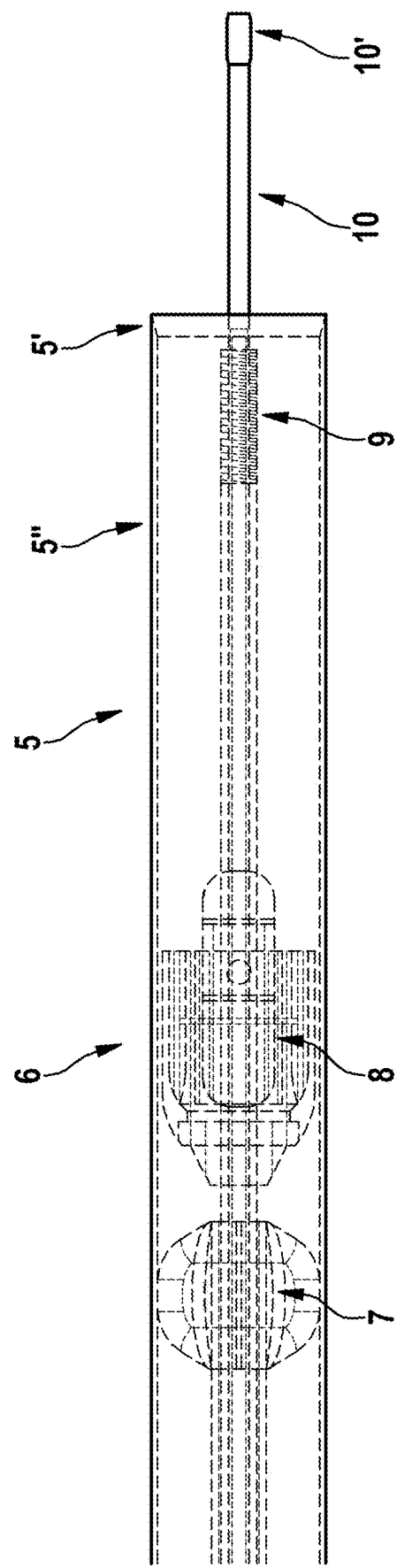

The invention will be better understood in the present chapter, with examples illustrated by the following figures:

FIG. 1 First example of a delivery system distal end (tip) according to the invention for an antegrade delivery system FIG. 1.1 Second example of a delivery system distal end (tip) according to the invention, represented by a balloon, for a retrograde delivery system FIG. 1.2 Third example of a delivery system distal end (tip) according to the invention for a retrograde delivery system FIG. 2 Example of a valve-cover with its components to retain the collapsed prosthetic valve FIG. 3 First example of a stopper to be placed inside the valve-cover. Its function is the retention of the crimped prosthesis during a retrograde implant procedure FIG. 3.1 Second example of a stopper to be placed inside the valve-cover showing the anchoring systems for the anterior and posterior engagement arms FIG. 3.2 Third example of a stopper to be placed inside the valve-cover showing the anchoring system for the anterior engagement arm FIG. 4 First example of a stopper to be placed inside the valve-cover. Its function is the retention of the collapsed prosthesis during an antegrade implant procedure (lateral view)

FIG. 4.1 Second example of a stopper, to be placed inside the valve-cover, for a delivery to be used during an antegrade implant procedure (front view)

FIG. 4.2 Third example of a stopper, to be placed inside the valve-cover, for a delivery to be used during an antegrade implant procedure (lateral and front views)

FIG. 5 First example of a hydraulic delivery system for a retrograde implant procedure FIG. 5.1 Second example of a hydraulic delivery system for a retrograde implant procedure (valve-cover separated from the shaft)

FIG. 5.2 Third example of a hydraulic delivery system for a retrograde implant procedure (valve-cover integrated with the shaft)

FIG. 6 First example of a mechanical delivery system for a retrograde or an antegrade implant procedure FIG. 6.1 Second example of a mechanical delivery system for a retrograde or an antegrade implant procedure (constructive details)

FIG. 6.2 Third example of another type of mechanical delivery system for an antegrade implant procedure FIG. 6.3 Fourth example of another type of mechanical delivery system for an antegrade implant procedure (constructive details)

FIG. 6.4 Fifth example of another type of hydraulic delivery system for an antegrade implant procedure (constructive details)

FIG. 7 Handle of a hydraulic delivery system (close view)

FIG. 7.1 Handle of hydraulic delivery system (general view)

Figure 8:
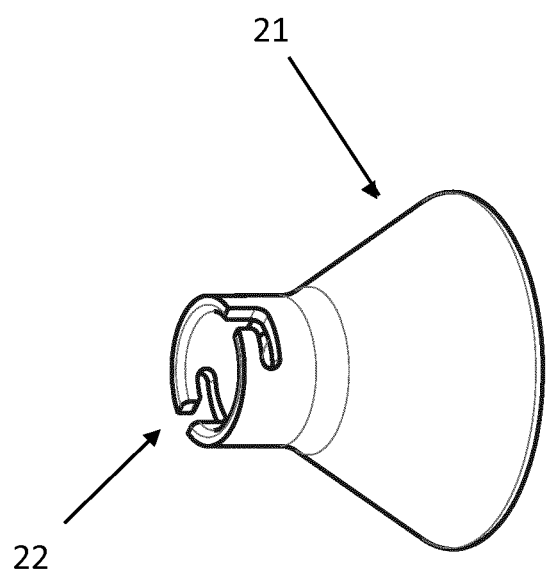

FIG. 8 First example of a round shape conical crimping element

Figure 9:
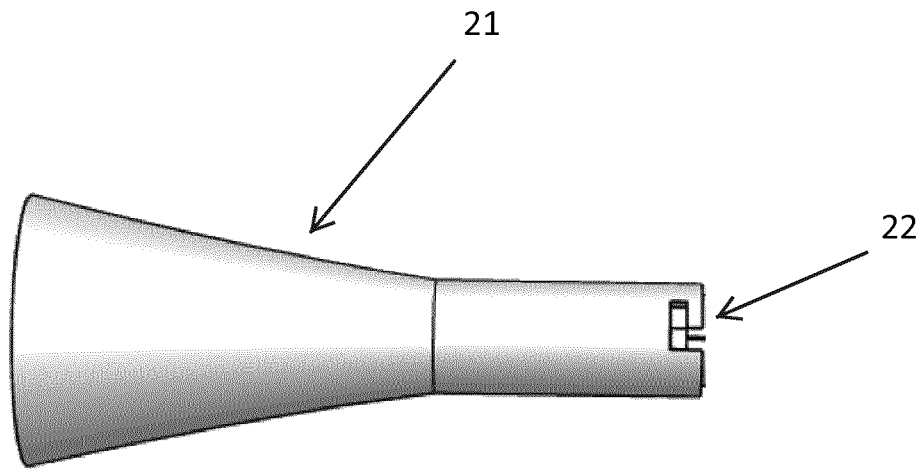

FIG. 9 Second example of a round shape conical crimping element (lateral view)

Figure 10:
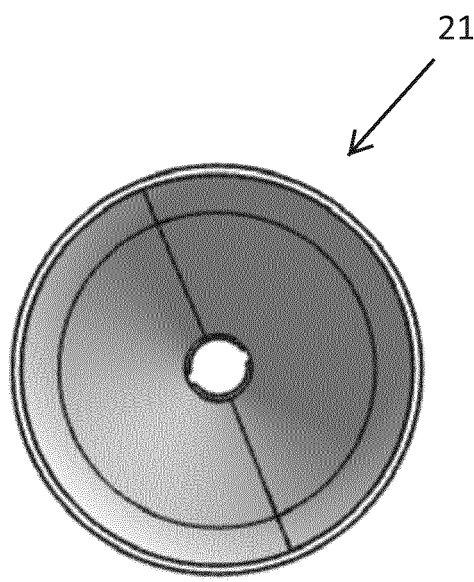

FIG. 10 Third example of a round shape conical crimping element (front view or insert side view)

Figure 11:
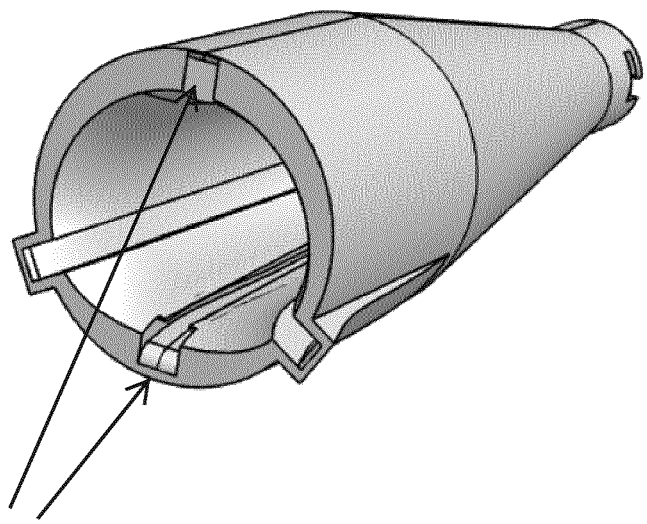
Figure 12:
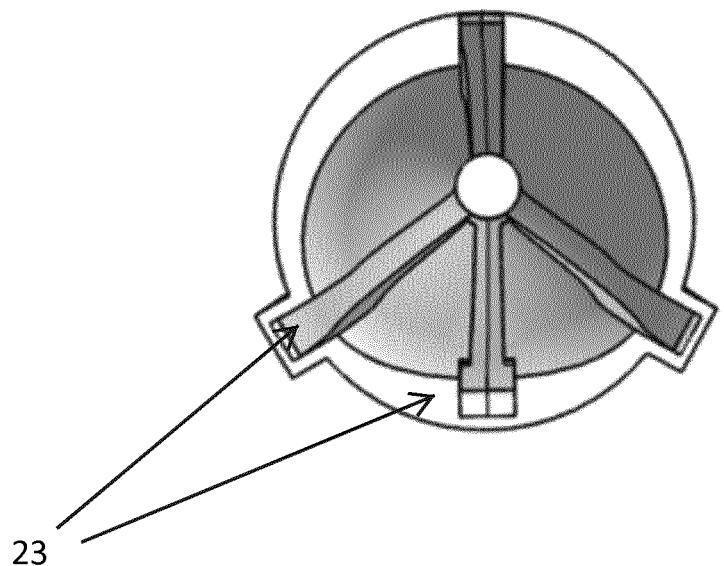

FIG. 11 Fourth example of a D-shape conical crimping tool with internal grooves FIG. 12 Fifth example of a D-shape conical crimping tool with internal grooves (front view)

Figure 13:
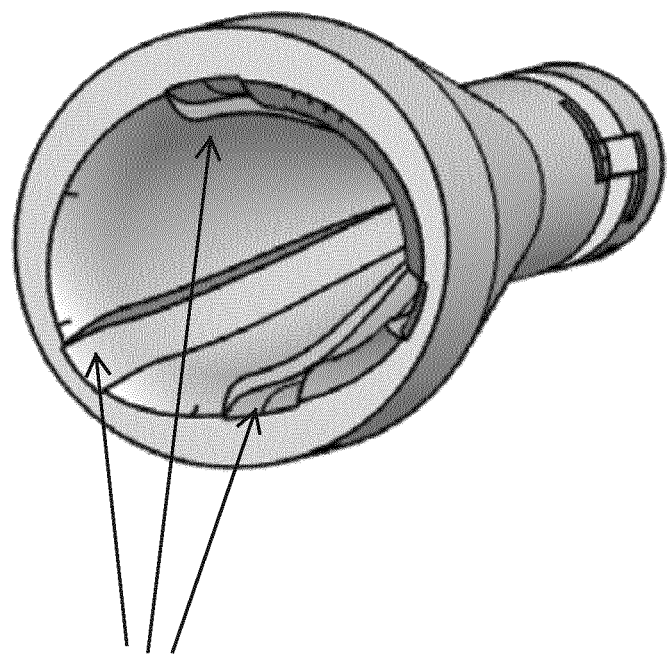

FIG. 13 Sixth example of a D-shape conical crimping tool with different type of internal grooves (front view)

Figure 14:
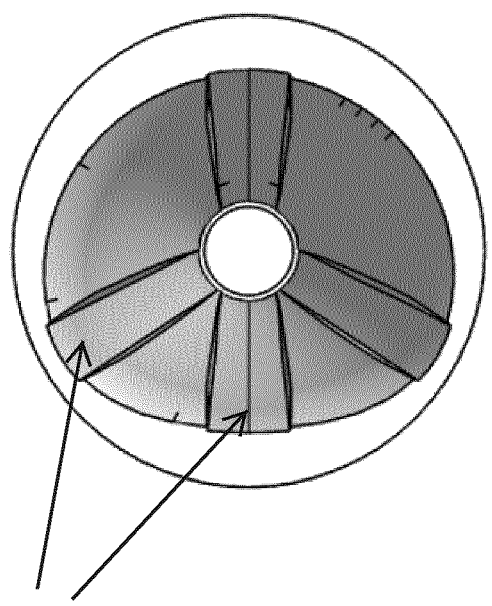

FIG. 14 Eight example of a D-shape conical crimping tool with different internal grooves (front view)

Figure 15:
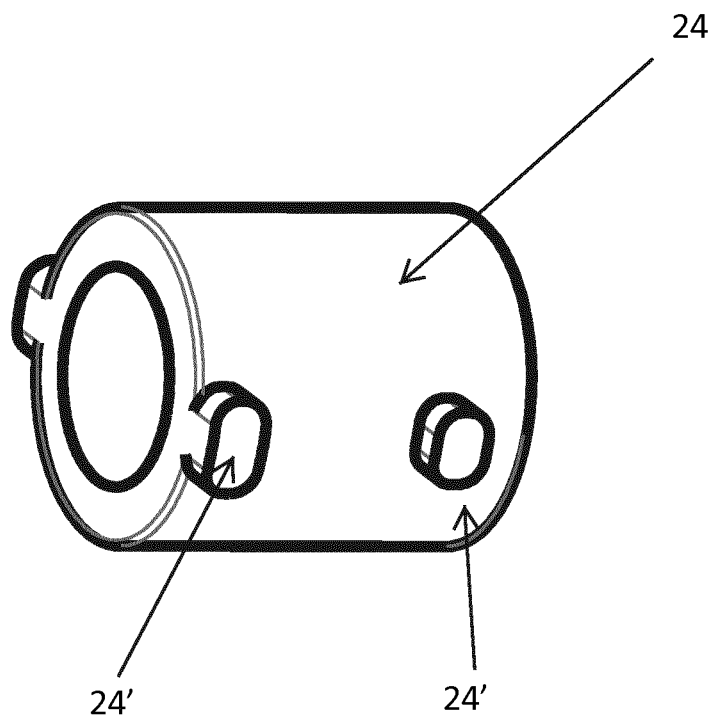

FIG. 15 Transfer tube

Figure 16:
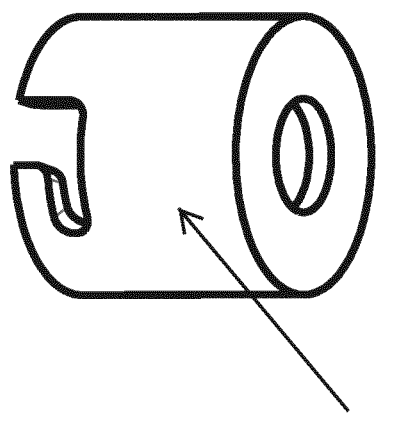

FIG. 16 Transfer tube cover cap

Figure 17:
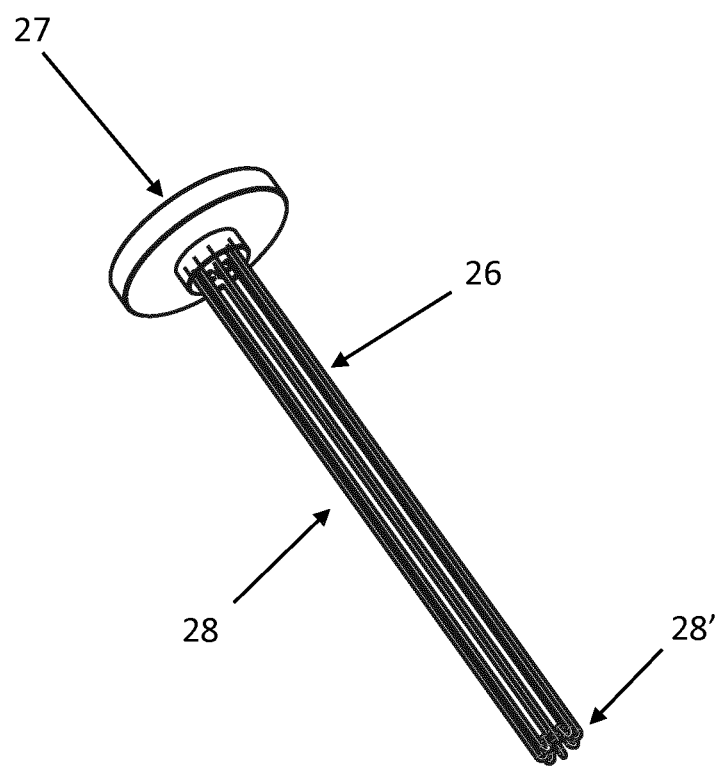

FIG. 17 First example of a pulling device

Figure 18:
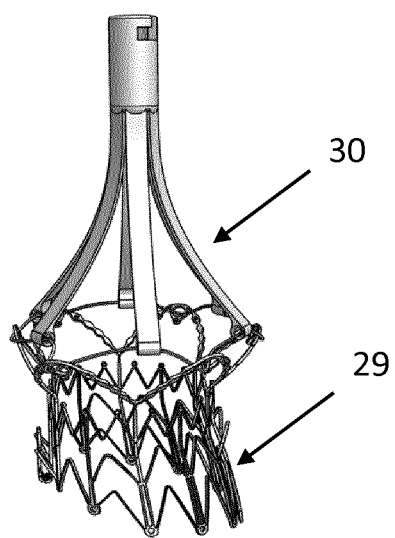

FIG. 18 Second example of a pulling device mounted on a valve prosthesis

Figure 19:
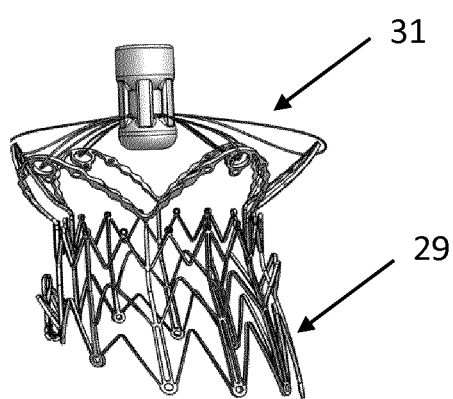

FIG. 19 Third example of a pulling device mounted on a valve prosthesis

Figure 20:
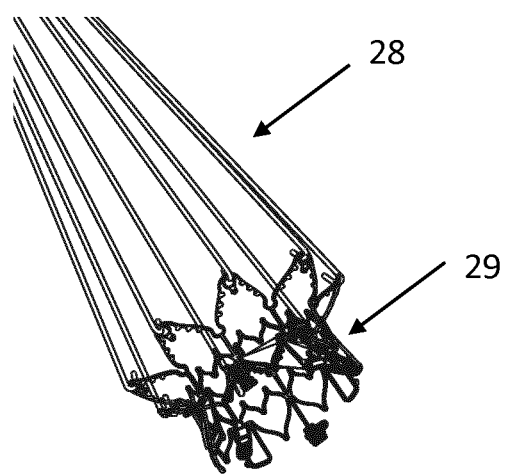

FIG. 20 Fourth example of a pulling device mounted on a valve prosthesis

Figure 21:
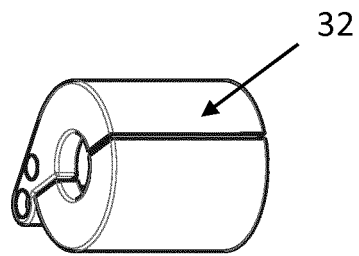

FIG. 21 Holding clamp

Figure 22:
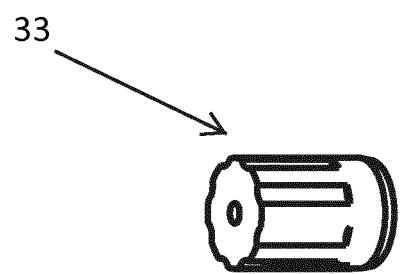

FIG. 22 Threaded locking cap

Figure 23:
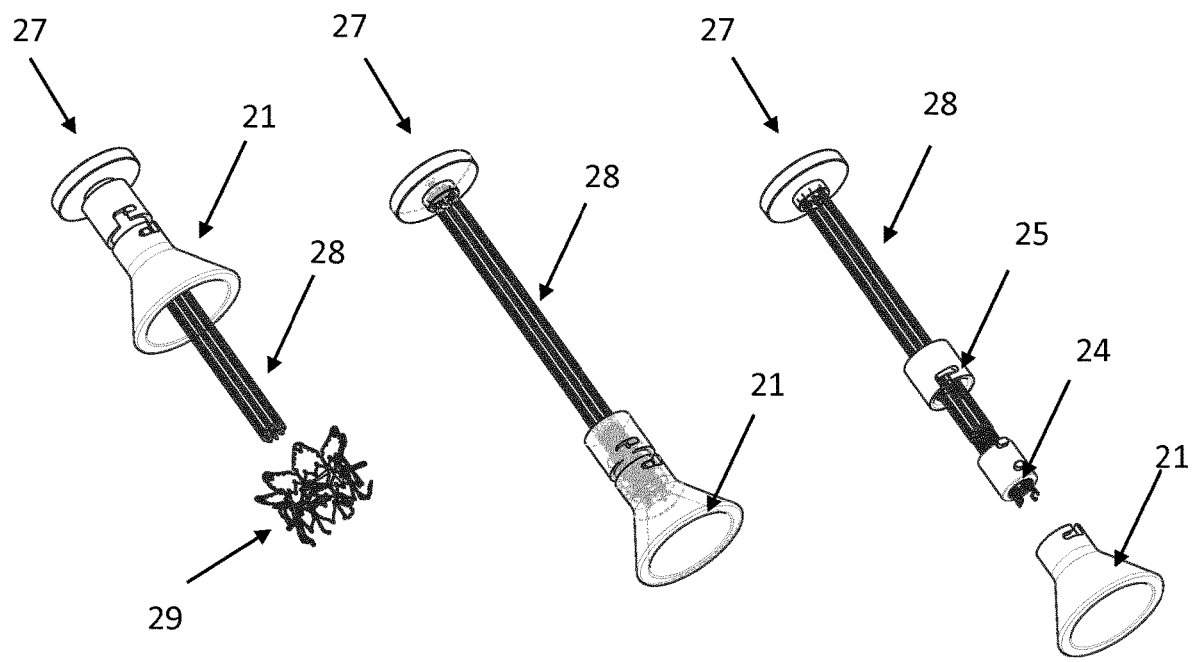
Figure 24:
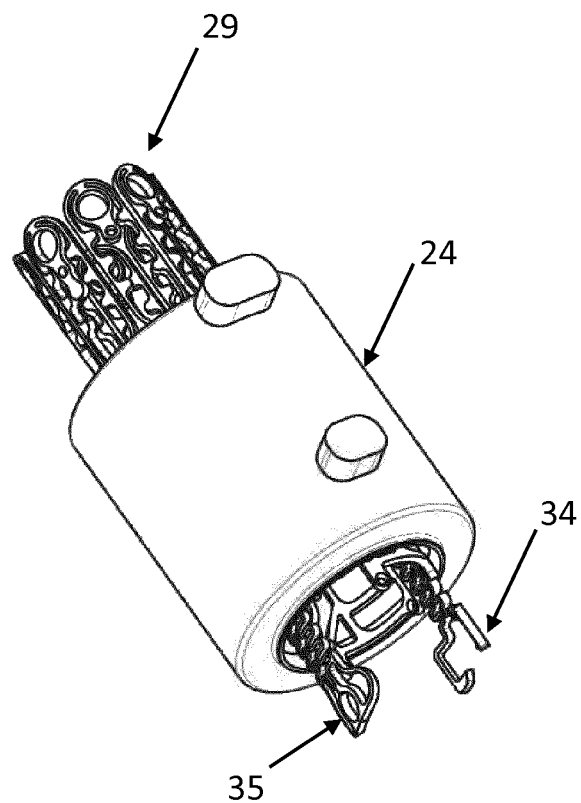
Figure 25:
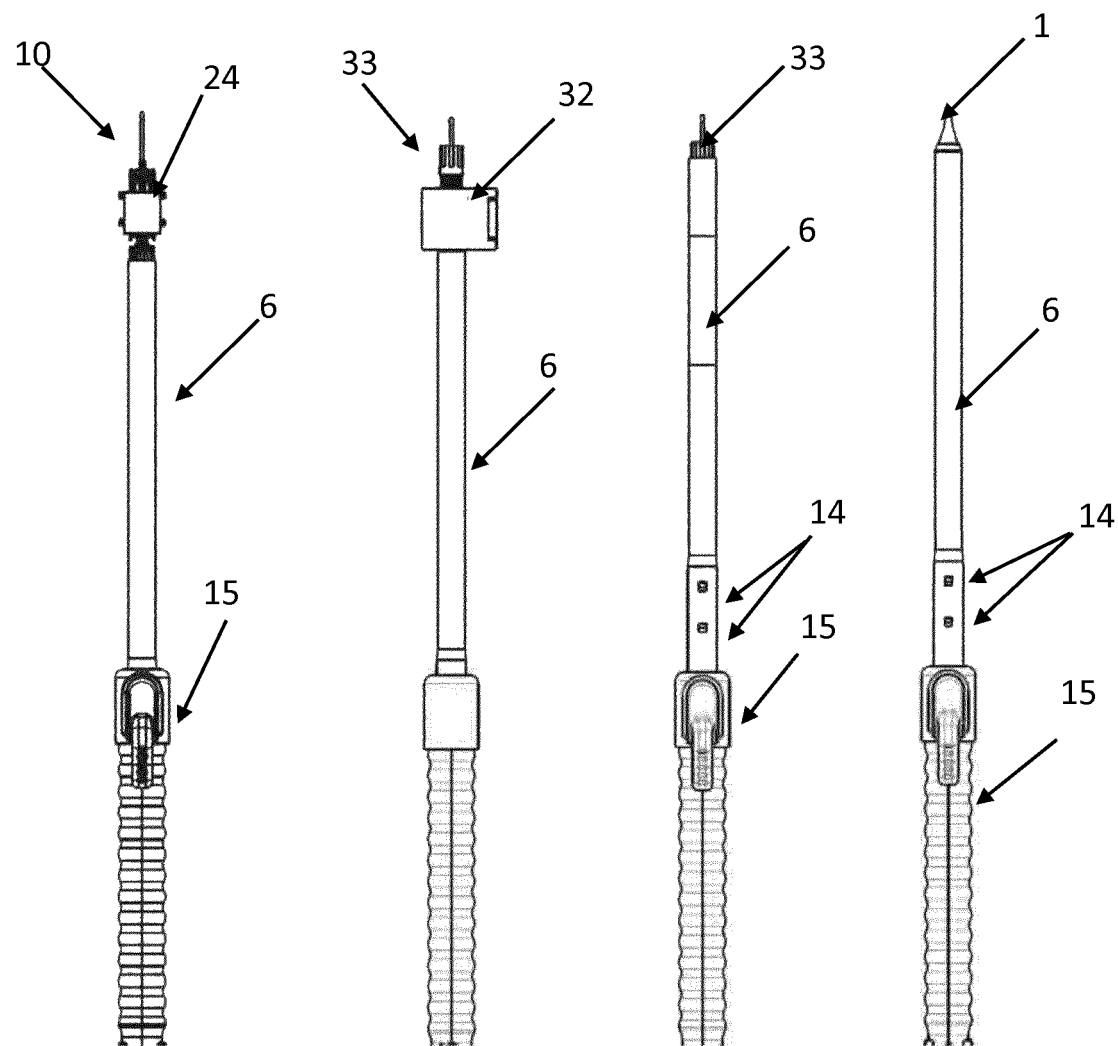

FIG. 23 Sequence representing the prosthesis loading into the crimping tool and final crimping procedure into the transfer tube FIG. 24 Transfer tube after crimping procedure with the collapsed prosthesis inside FIG. 25 Loading procedure of the collapsed prosthesis into the delivery system

NUMERICAL REFERENCES UNSED IN THE FIGS.

1. Delivery system distal tip for a delivery system used in a retrograde implant procedure 1'. Purging holes for debubbling of the delivery system 1". Sealing balloon acting a s a tip 1'''. Delivery system distal tip for a delivery system used in an antegrade implant procedure 2. Conical part of the tip 3. Gasket to seal the seal the tip with the delivery shaft 4. Lumen of the tip (guidewire lumen)

5. Valve-cover of delivery shaft

5'. Distal edge of the delivery shaft with radiopaque marker

5". Radiopaque marker on the delivery shaft

6. Delivery shaft

7. Spacer inside the delivery shaft to avoid kinking of the shaft

8. Valve retention element or Stopper for a retrograde delivery system

8'. Valve retention element or Stopper for an antegrade delivery system 9. Male crank onto which is screwed the threaded demale portion of the tip 9'. Threaded female portion of the tip 10. Inner shaft of the delivery system (during implant procedure it contains the guidewire)

10'. Radiopaque tip of the inner shaft

11. Anterior anchoring element of the stopper

12. Posterior anchoring element of the stopper

13. First example of anchoring pins for the atrial petals of the prosthesis on a stopper for antegrade delivery system 13'. Second example of anchoring pins for the atrial petals of the prosthesis on a stopper for antegrade delivery system 13". Stopper grooves for accommodation of atrial petals of the prosthesis for an antegrade delivery system 14. Grooves for the release lock control in a hydraulic delivery system 14'. Ring acting as a lock control in a mechanical delivery system 15. Release lock control 16. System safety lock 17. First example of a delivery system handle 17'. Second example of a delivery system handle 18. First example of an actuation trigger in a mechanical delivery system 18'. Second example of an actuation trigger in a mechanical delivery system 19. Rotational ratchet to achieve a good rotational orientation of the prosthesis during deployment in a mechanical delivery system 20. Proximal ports for guidewire entrance and injection of fluids (radiopaque medium, etc.)

21. Conical crimping element used for collapsing the prosthesis

22. Quick connection system

23. Grooves inside the round and D-shape conical crimping elements

24. Transfer tube

24'. Anchoring pins on transfer tube

25. Transfer tube secure cap

26. Pulling device

27. Holder part of the pulling device

28. First example of rigid elements of the pulling device

28'. Anchoring system at the distal end of the pulling device

29. Example of valve prosthesis

30. Second example of rigid elements of the pulling device

31. Third example of rigid elements of the pulling device

32. Holding clamp to retain the prosthetic engagement arms during the loading procedure of the prosthesis into a retrograde delivery system 33. Threaded locking cap to maintain closed the atrial flange petals of the prosthesis during the loading procedure of the prosthesis into a retrograde delivery system 34. Posterior engagement arm of the prosthesis 35. Anterior engagement arm of the prosthesis Delivery System The delivery system preferably uses a hydraulic (FIG. 5), mechanical (FIG. 6, 6.1, 6.2, 6.3), electric or hybrid (both hydraulic and mechanical motion systems together) actuation mechanisms.

In these different actuation mechanisms, several features are maintained equal (the tip, the valve-cover and the shaft). The delivery system consists in a proximal elongated structure 17 called handle (that includes the actuation mechanism for the deployment of the prosthesis) and a distal structure constituted, in distal to proximal direction, by a tip 1, 1" and 1''' (FIGS. 1, 1.1 and 1.2), a valve-cover 5 (where the valve is loaded before releasing into the heart) and a transparent shaft 6 (FIG. 2, 5, 5.1, 5.2, 6, 6.2, 6.3, 6.4). In one embodiment (FIG. 5.2) the valve-cover 5 is integrated into the shaft 6 in one single piece. The most distal part of the system is equipped with a soft polymeric tip 1, 1''' or a balloon-tip 1". Inside the system (FIG. 7) is channeled an inner metallic pipe 10 which allows the introduction of the guiding wire used during implant procedure and flushing of fluids.

Four main parts successively compose the delivery system as described in FIG. 2, 5, 5.1, 5.2, 6, 6.2, 6.3, 6.4:

the distal tip 1, 1" and 1''', the valve-cover 5 and the valve retention element 8 called stopper, the shaft 6, the handle 17, carrying on the moving parts such as the hydraulic, mechanic, electric or hybrid actuation systems, the different proximal ports 20, the prosthesis release lock control 15 (during implant procedure) engaging in the grooves 14 and the system safety lock 16 preventing the unwanted release of the valve (before starting the prosthetic valve deployment).

Delivery Tip, Stopper and Valve Cover

On the distal end (FIG. 1), the delivery system is provided with a conically shaped soft tip 1 made of a flexible polymeric material (silicon or polyurethane or other biocompatible polymers eventually loaded with radiopaque materials).

The soft tip 1, 1''' are anchored to a metallic or polymeric basement 2 that must fit and seal on the valve-cover 5. The sealing is obtained via a gasket 3 positioned at the bottom of basement 2. In the soft tip 1 purging holes 1' are created to allow the expulsion of air bubbles during the purging procedure.

The soft tip is mounted on the delivery inserting it over the inner shaft 10 that exits from the lumen 4 (FIG. 1, 1.2). The proximal female portion of the tip 9' is screwed on the crank 9 placed on the inner shaft 10 of the delivery system (FIG. 2). After the prosthesis has been loaded, the delivery tip perfectly seals the valve-cover 5 by means of the gasket 3 (FIG. 1, 1.2).

The tip 1, 1''', before starting the implant procedure, allows the sealing of the valve-cover 5 so that a purging procedure from air bubbles with sterile saline solution can be completed. The saline solution is injected from a proximal port 20, placed at the bottom of the handle 17, with the aim to purge out the air bubbles from the valve-cover 5 through small holes 1' (from two to four) so that avoiding the risk of air embolization during bioprosthetic valve deployment.

During the implant procedure the shape and the softness of the tip 1, 1''' is particularly important. It allows a gentle and smooth entrance of the delivery system into the heart chambers (atria or ventricles) across the myocardial wall without damaging it.

In one embodiment (FIG. 1.1, 6.2, 6.3) that may be advantageously used for antegrade implant access (transatrial or transseptal), the distal portion of the delivery system has the shape of a balloon 1" similar to those used for angioplasty catheter procedures. This balloon-tip is inflated with a radiopaque medium before the procedure. It allows, when inflated, a perfect sealing of the tip over the valve-cover 5 preventing the entrance of air bubbles and making atraumatic the distal part of the delivery device while crossing the anatomical structures such as ventricles, atria and inter-atrial septum. The adoption of a balloon-tip for the distal portion is extremely important for the antegrade approach since during retrieval of the delivery, after the deployment of the valve, the tip can be deflated avoiding any possible entrapment with the valve's leaflets.

Before implant, the prosthetic valve is collapsed down with a specific crimping tool and loaded inside the valve-cover 5 (FIG. 2, 5, 5.1, 5.2, 6, 6.2, 6.3, 6.4) located on the distal portion of the delivery system. It consists in a cylindrical chamber usually made of a thin but rigid polymeric and transparent material resistant enough to contain the radial force of the collapsed prosthesis with minimal deformation. In alternative embodiments the valve-cover can be still rigid but realized in metal alloy in order to keep it very thin. In another inventive solution the valve-cover can be realized in very thin (e.g. thinner than 100 μm), flexible and radially non-compliant polymeric material (similar to the balloon angioplasty catheters); this valve-cover can have a variable thickness with a thicker portion starting from the distal edge where a radiopaque ring is placed and where a good fitting with a rigid tip or a balloon tip is needed. A thin and flexible valve-cover is particularly useful for transseptal antegrade delivery systems where a steering of the delivery shaft is present. During the implant procedure the valve cover is retracted to deploy the valve and if it is thick and rigid it could interfere with a regular deployment of the prosthesis. Therefore a thin and flexible valve-cover avoids any interference, during the deployment procedure, with the proximal portion of the delivery shaft where steering is present. The thickness and flexibility of the valve cover can be continuous or discontinuous; can vary in steps or segments from the proximal to the distal portion of the valve-cover and in any other combination thereof. Radiopaque markers 5' are positioned both circumferentially and radially along the valve-cover 5 allowing a correct orientation and positioning of the valve during implant. In order to safely retain the prosthesis inside the valve-cover 5, the same is anchored to a retainer called stopper 8 (FIG. 2).

When the valve is loaded the stopper 8 is positioned at the proximal end of the valve-cover 5 and it is mounted over the inner shaft 10 of the delivery that crosses all the delivery length (FIG. 2). The inner shaft 10 is a metallic pipe that crosses all delivery system from its distal to proximal ends. The distal portion 10' is made of a radiopaque material so that the maximal protrusion of the delivery is always known during the implant procedure (FIG. 2). On the distal portion of the shaft 10 is also present a crank 9 on which the tip 1, 1''' is screwed through the female thread 9'.

The stopper design changes depending on the antegrade or retrograde type of implant access (FIG. 3, 3.1, 3.2, 4, 4.1, 4.2).

The stopper 8 has the function to retain the prosthesis during the loading phase into the valve-cover 5. It has also the function to impede the prosthesis jumping out from the valve-cover before the prosthesis deployment is completed.

For a left ventricle transapical approach (retrograde), the valve prosthesis is retained to the stopper 8 by anchoring the ventricular portion (outflow side) of the prosthesis to specifically designed anchoring elements 11 and 12 of the stopper. In particular, the stopper, here represented, is designed with two different opposite anchoring elements 11, 12 (FIG. 3, 3.1, 3.2). The shape and number of anchoring elements depends on the anterior or posterior turning engagement arms present on the prosthetic stent. Two pins element 12 (FIG. 3, 3.1) is dedicated to anchoring the posterior ventricular engagement arm of the prosthesis (when the valve is deployed the engagement arm turns-up to almost 180° to grab the posterior native mitral leaflet). The opposite pin with a flat portion 11 (FIG. 3, 3.1, 3.2), present on the stopper 8, is dedicated to anchoring the anterior ventricular engagement arm of the prosthesis (when the valve is deployed it can turn up to 180° to grab and block the anterior native mitral leaflet). Both different anchoring pins 11 and 12 are specially designed to retain the valve prosthesis when the valve engagement arms are in flat position after the bioprosthesis has been crimped.

The stopper 8 is realized with resistant materials such as metal alloys (stainless steel, titanium, etc.) obtained by machining or by laser syntherization of metal powders or other technologies. In alternative, it can be realized by moulding, laser syntherization or machining of high resistant polymers.

In order to keep flat the anterior engagement arm, the stopper is provided with an extension element 11 (FIG. 3, 3.1, 3.2).

The anterior extension element of the stopper also allows the operators to identify the anterior side of the prosthesis inside the valve-cover under X-ray imaging during the implant procedure.

In case of transatrial or transseptal approach or so called antegrade approach, the stopper 8 is provided with eight pins 13 (typically 6 to 12) allowing the prosthesis to engage into specific holes present on the atrial flange of the prosthesis (prosthetic inflow side) (FIG. 4, 4.1, 4.2).

Delivery Shaft

The delivery shaft 6 is one of the features maintained equal in different delivery systems here described. It consists in a biocompatible and possibly transparent pipe connecting the handle 17, 17' with the valve-cover.

The delivery shaft 6 must be relatively flexible, eventually steerable at different degrees depending on the adopted implant procedure (retrograde or antegrade), provided with longitudinal and/or circumferential radiopaque markers 5' to guide the operators during the implant procedure (FIG. 2, 5, 5.1, 5.2, 6, 6.1, 6.2, 6.3, 6.4).

The longitudinal markers 5" allow the correct alignment of the crimped prosthesis, with respect to the longitudinal radiopaque marker lines during the loading procedure and it is mandatory for a correct positioning during implant.

The circumferential radiopaque marker 5' is placed at the distal end of the valve-cover. It is a radiopaque metal ring or paint (tantalum, tungsten or other similar radiopaque metals) embedded in the polymeric material of the valve-cover 6. This marker 5' allows the operator to evaluate the position of the distal end the valve-cover during the implant procedure.

The shaft 6 is connected to the valve-cover 5 by a connection element (FIG. 5.1) or the shaft and valve-cover are obtained from one single piece of tube (FIG. 5.2, 6, 6.2, 6.3, 6.4). This second embodiment completely avoids possible discontinuities between the connection parts making the system smoother and easier to manufacture.

In order to enhance the easiness of the valve deployment during the implant procedure the outside surfaces of the shaft 6 can be coated with a hydrophilic material.

Handle

The handle 17 controls the loading and the deployment of the prosthesis before and during the procedure. Different handle systems may be used respectively for mechanic, hydraulic or hybrid systems.

In one embodiment, the mechanism used to load and deploy the valve is hydraulic (FIG. 7). One hydraulic system solution could be composed by a hydraulic piston used through a compression chamber (FIG. 7.1) that allows the motion of the stopper 8 through the valve-cover 6 (FIG. 5.1, 5.2, 6.4).

In another embodiment (FIG. 6), the actuation mechanism, used to load and deploy the valve, is mechanical. The mechanical solution is composed by a rack movement system (FIG. 6.1) that allows the motion of the stopper 8 through the valve-cover 6.

The handle of the mechanical delivery system is characterized by having a handle 17' and an actuation trigger 18 that moves the shaft back and forth during the deployment and loading procedure of the prosthesis. As described for the hydraulic delivery system the mechanically operated handle is also provided with the different ports 20 for purging and introduction of the guidewire, the prosthesis release control 15 (during implant procedure) and the system safety lock 16 preventing the unwanted release of the valve (before the implant procedure).

Another example of mechanical delivery system is represented in FIGS. 6.2 and 6.3. The movement is granted by an endless screw, in direct continuity with the handle 17, onto which is turning a knob 18'. The release lock control is obtained with a positionable ring 14'. This mechanical movement, instead to be manually controlled, can be also actuated by a linear electric motor.

In another embodiment, the actuation system is hybrid and uses the mechanical movements, above described, to load the valve into the delivery system and a hydraulic one to deploy the valve in position or vice-versa.

The handle is provided with two different buttons or switches aimed at safely control the implant procedure (the prosthesis release control 15 and the system safety lock 16.

The prosthesis release control 15 (FIG. 5, 5.1, 5.2) is located at the distal end of the hydraulic handle and allows an accurate control of the deployment procedure releasing the valve at predefined steps. The release control mechanism is designed in order to deploy the valve prosthesis at specific and predefined steps. In the mechanical actuated system the prosthesis release control is placed on the upper part of the handle 17' (FIG. 6, 6.1).

In one embodiment the system safety lock 16 (FIG. 5) is located at the proximal end of the hydraulic delivery system and at the proximal end of the mechanical delivery system (FIG. 6, 6.1, 6.2, 6.3). It impedes any unwanted accidental release of the prosthesis before the correct positioning is obtained.

In another embodiment (FIG. 6, 6.1) the actuation of a rotational ratchet 19 allows a rotational movement of the valve-cover.

The handle 17, 17' may also be equipped with one or two hub connections. One is placed at the proximal end of the handle and allows the entrance of the guide wire and the lumen flushing with saline or contrast medium (FIG. 5, 6, 6.1, 6.2, 6.3, 6.4). The second one is grouping three different pressure lines dedicated to the loading, release and purging of the entire system. This second hub connection is placed on the handle 17, 17' and allows the entrance of liquid ensuring the movement of the piston (for the hydraulic handle) and also allows the purging procedure before the valve is implanted.

The second hub connection could be also positioned on the handle for the mechanical solution (FIG. 6, 6.1). In this solution the hub connection only allows only the purging procedure before the valve is implanted.

All four versions of the actuation system offer the possibility to perform the purging of the delivery from air bubbles prior its introduction in the heart. Such mechanism prevents the introduction of unwanted air bubbles embolization in the circulatory system, thus leading to the occurrence of potentially critical cerebral vascular accidents.

Crimping Tool

As mentioned previously, the crimping tool is designed to collapse the prosthetic valve within the system, and more precisely inside the valve-cover 5.

The same crimping tool may be used with all four types of delivery systems (mechanic, electric, hydraulic and hybrid).

Three main parts compose the crimping tool.

The first part is composed by a conical crimping element 21 (FIG. 8-14) that reduces the valve diameter from the unexpanded size to the crimped size (it is different size by size).

The conical crimping element 21 can be smooth inside (FIG. 9, 10) or machined inside to obtain several grooves 23 along its length to accommodate the anchoring systems of the prosthesis. (FIGS. 11 to 14).

In other embodiments, the conical crimping element may have a D-shape or a circular shape with an internal profile changing at different lengths. The conical crimping element 21 ends at one side with a quick connection system 22 (FIG. 8) to connect with the transfer tube 24.

The second part is made of two elements: a cylindrical tube element called transfer tube 24 (FIG. 15) and a transfer tube secure cap 25 (FIG. 16). The transfer tube 24 is connected, from one side via two ore more pins 24' at the conical crimping element and from the other side to the transfer tube secure cap 25.

In another embodiment (not illustrated) the second part only consists of a transfer tube, i.e. there is no secure cap.

The third main part is composed by a pulling device 26 (FIG. 17) used to pull the valve through the conical crimping element 21, the transfer tube 24 and until reaching the secure cap 25. The pulling device is composed by a metal or plastic support from which come out two to eight rigid elements 28 with an anchoring system at the distal end 28'. The pulling device has a holder part 27 to allow the operator to pull the prosthesis during the crimping procedure.

In one embodiment, the pulling device 26 contains hooks 28' to hold the prosthesis at level of the atrial flange (FIG. 17). Alternatively, the pulling device 26 has a specific holding system designed to make easier the load and release of the device from the prosthesis during the crimping procedure.

In other embodiments, the pulling device 26 acts as pull holder systems 30 and 31 that capture a yarn passed through holes placed at the proximal end of the prosthetic atrial flange 29 of the prosthesis (FIG. 18, 19, 20). This anchoring solutions, in preparation of the crimping procedure, are suitable for all implants made via antegrade and retrograde procedures. In fact crimping the prosthesis inside the transfer tube, pulling it from the atrial flange, allows to load the prosthesis into the delivery system for both antegrade and retrograde procedures.

The pulling device can be also anchored to the prosthesis 29 by means of solid and flexible wires or bands 30 grabbing the atrial flange of the prosthesis 29 (FIG. 18).

Another embodiment the pulling device may capture a valve holder element already fixed at the atrial side of the prosthesis (FIG. 19) by means of yarns 31 anchored in holes at the proximal end of the prosthetic atrial flange 29.

The same pulling device 26, adequately modified, is attached to the atrial flange of the prosthesis 29 by means of rigid elements 28 (FIG. 20).

Additional tools needed for the prosthesis crimping procedure are the holding clamp 32 (FIG. 21) and the cylindrical threaded locking cap 33 (FIG. 22).

Crimping Procedure

The crimping procedure is described in FIG. 23. The pulling device 26 is inserted into the conical crimping element 21 previously mounted together with transfer tube 24 and transfer tube secure cap 25. The atrial flange of prosthesis 29 is then anchored to the pulling device 26 by means of anchoring hooks 28' as part of rigid elements 28. Acting on the holder 27 the prosthesis 29 is pulled inside the mounted conical crimping device 21 until reaching a stop to the transfer tube secure cap 25 inside the transfer tube 24.

The prosthesis 29, in crimped position, inside the transfer tube 24 is illustrated in FIG. 24. The atrial portion of the prosthesis (atrial petals) is exposed as well as the ventricular engagement arms 34 and 35.

The loading procedure of the crimped prosthesis for example into the retrograde hydraulic delivery system 16 is described in FIG. 25 (transapical procedure). The prosthesis collapsed (atrial side up for retrograde implant procedure) inside the transfer tube 24 is inserted through the internal shaft 10 until the engagement arms 34 and 35 approximate and engage the stopper 8. The holding clamp 32 is then mounted over the engagements arms 34, 35 to keep them straight and keep straight respectively the structures 11 and 12 placed on the stopper 8. The threaded locking cap 33 is then screwed on 10' blocking the atrial petals. The holding clamp 32 is then removed and meanwhile the valve-cover/shaft 5, 6 is advanced the loading of the prosthesis is completed. When the loading is almost completed the threaded locking cap 33 is unscrewed from the internal shaft 10 and removed. Screwing the tip 1 on the crank 10' completes the prosthesis loading procedure. Immediately after the prosthetic valve loading into the delivery system and before the implant, a system debubbling procedure is performed.

It should be mentioned that the conical element 21 and the transfer tube secure cap 25 are used in the crimping procedure but no more in the loading procedure, as shown on FIGS. 23 and 25.

The invention is of course not limited to the illustrated examples but encompasses any alternative object that is defined by the claims.

The invention claimed is:

1. A transcatheter delivery system comprising: a handle; a hollow shaft; a distal tip, a self-expandable heart valve prosthesis;
   an actuation mechanism for moving the hollow shaft towards the distal tip or the handle, the hollow shaft configured to slidingly receive the self-expandable valve prosthesis in a compressed state; and
   a valve prosthesis crimping tool including a hollow conical element; a detachable transfer tube; and a pulling device,
   wherein the hollow conical element is configured to allow the self-expandable valve prosthesis to enter in an expanded state through a base of the hollow conical element, and enter the transfer tube in the compressed state, wherein the valve prosthesis comprises a valve prosthesis anchoring system and the hollow conical element comprising at least one longitudinal groove for accommodating the valve prosthesis anchoring system, wherein the at least one longitudinal groove has an open end at an extremity of the conical element, wherein the longitudinal groove starts at a terminal face of an open end of the hollow conical element, and
   wherein the self-expandable valve prosthesis is configured to be pulled by the pulling device when crossing the hollow conical element and entering the detachable transfer tube, the detachable transfer tube configured to be temporarily connected to the hollow conical element.

2. The delivery system according to claim 1, wherein the conical element has a non-circular cross section at a first extremity.

3. The delivery system according to claim 2, wherein the conical element has a substantially circular cross section at a second extremity.

4. The delivery system according to claim 1, wherein the pulling device is configured to capture a valve holder already fixed to the valve prosthesis.

5. The delivery system according to claim 1, wherein the at least one longitudinal groove comprises a closed outer wall.

6. The delivery device according to claim 1, wherein the number of grooves is selected from the group comprising: at least two longitudinal grooves, at least three longitudinal grooves, at least four longitudinal grooves.

7. The delivery system according to claim 1, further comprising: a transfer tube secure cap configured to be temporarily connected to the detachable transfer tube.

8. The delivery system according to claim 1, further comprising: a stopper that is configured to hold the self-expandable valve prosthesis within the hollow shaft.

9. The delivery system according to claim 1, further comprising: a valve-cover that is located between the hollow shaft and the distal tip.

10. The delivery system according to claim 1, wherein the actuation mechanism includes a mechanical or electric or hydraulic actuation device.

11. A transcatheter delivery system for a self-expandable heart valve prosthesis comprising: a handle; a hollow shaft; a distal tip;

an actuation mechanism for moving the hollow shaft towards the distal tip or the handle, the hollow shaft configured to slidingly receive the self-expandable valve prosthesis in a compressed state; and a valve prosthesis crimping tool including, a hollow conical element; a detachable transfer tube; and a pulling device, wherein the hollow conical element is configured to allow the self-expandable valve prosthesis to enter in an expanded state through a base of the hollow conical element, and enter the transfer tube in the compressed state, wherein the pulling device is configured to capture a valve holder already fixed to the valve prosthesis, wherein the delivery system comprises a transfer tube secure cap configured to be temporarily connected to the hollow conical element at a proximal longitudinal side of the transfer tube on an opposing side with respect to an open end of the hollow conical element, and wherein the self-expandable valve prosthesis is configured to be pulled by the pulling device when crossing the hollow conical element and entering the detachable transfer tube until reaching the transfer tube secure cap, the detachable transfer tube configured to be temporarily connected to the hollow conical element.

12. The delivery system according to claim 11, wherein the pulling device is configured to capture the valve holder already fixed to the atrial side of the valve prosthesis.

13. The delivery system according to claim 11, wherein the pulling device is configured to capture the valve holder, the valve holder already fixed to the valve prosthesis by means of yarn.

14. The delivery system according to claim 11, wherein the pulling device is configured to capture the valve holder, the valve holder already fixed to the valve prosthesis by means of rigid elements.

15. The delivery system according to claim 11, wherein the conical element has a non-circular cross-section at a first extremity and a substantially circular cross-section at a second extremity.

16. The delivery system according to claim 11, wherein the conical element has at least one longitudinal groove for accommodating an anchoring system of a valve prosthesis, further wherein the at least one longitudinal groove has a closed outer wall.

17. The delivery system according to claim 11, further comprising: a valve-cover that is located between the hollow shaft and the distal tip.

18. The delivery system according to claim 11, further comprising: a stopper that is configured to hold the self-expandable valve prosthesis within the hollow shaft.

19. The delivery system according to claim 11, wherein the actuation mechanism includes a mechanical or electric or hydraulic actuation device.

* * * * *